United States Patent
Froehlich et al.

(10) Patent No.: US 9,149,935 B2
(45) Date of Patent: Oct. 6, 2015

(54) HANDLING DEVICE AND METHOD FOR OPERATING A HANDLING DEVICE

(71) Applicant: Deutsches Zentrum Fuer Luft-Und Raumfahrt E.V., Cologne (DE)

(72) Inventors: Florian Alexander Froehlich, Germering (DE); Stefan Joerg, Munich (DE)

(73) Assignee: Deutsches Zentrum Fuer Luft-Und Raumfahrt E.V., Linder Hoehe, Cologne ( * ) Notice: Subject to any disclaimer, the term of this patent is extended or adjusted under 35 U.S.C. 154(b) by 0 days.

(21) Appl. No.: 14/346,526

(22) PCT Filed: Sep. 26, 2012

(86) PCT No.: PCT/EP2012/068955
§ 371 (c)(1),
(2) Date: Mar. 21, 2014

(87) PCT Pub. No.: WO2013/045489
PCT Pub. Date: Apr. 4, 2013

(65) Prior Publication Data
US 2014/0229009 A1    Aug. 14, 2014

(30) Foreign Application Priority Data

Sep. 28, 2011  (DE) .......................... 10 2011 115 077

(51) Int. Cl.
*G05B 15/00*  (2006.01)
*G05B 19/00*  (2006.01)
(Continued)

(52) U.S. Cl.
CPC ............. *B25J 15/04* (2013.01); *A61B 19/2203* (2013.01); *A61B 2017/00482* (2013.01); *A61B 2019/4842* (2013.01)

(58) Field of Classification Search
CPC ................ B25J 15/04; A61B 16/2203; A61B 2017/00482; A61B 2019/4842
USPC ........ 700/245, 257, 264; 318/568.11, 568.12, 318/568.14, 568.21
See application file for complete search history.

(56) References Cited

U.S. PATENT DOCUMENTS 6,071,281 A  *  6/2000  Burnside et al. ................ 606/41
6,981,941 B2 *  1/2006  Whitman et al. ................ 600/1
(Continued)

FOREIGN PATENT DOCUMENTS

EP  2486862 A2 *  8/2012  ........... A61B 17/115
JP  2009117732 A   5/2009

OTHER PUBLICATIONS

International Search Report dated Jan. 23, 2013 for PCT application No. PCT/EP2012/068955.
(Continued)

*Primary Examiner* — Dalena Tran
*Assistant Examiner* — Jaime Figueroa
(74) *Attorney, Agent, or Firm* — Ohlandt, Greeley, Ruggiero & Perle, LLP

(57) ABSTRACT

A handling device, which is in particular a robot, has a receiving device for receiving different instruments. To this end, the receiving device and the different instruments have mutually compatible connecting elements. In order to ensure error-free connection of the correctly selected instrument to the receiving device, the instruments have changeable indicator devices. The indicator devices are changed with the aid of a control device, for example on the basis of a schedule.

9 Claims, 3 Drawing Sheets

(51) Int. Cl.
  *B25J 15/04* (2006.01)
  *A61B 19/00* (2006.01)
  *A61B 17/00* (2006.01)

(56) References Cited

U.S. PATENT DOCUMENTS

| | | | |
|---|---|---|---|
| 7,763,015 B2* | 7/2010 | Cooper et al. | 606/1 |
| 7,896,815 B2* | 3/2011 | Thrope et al. | 600/554 |
| 2006/0095096 A1* | 5/2006 | DeBenedictis et al. | 607/88 |
| 2006/0167440 A1* | 7/2006 | Cooper et al. | 606/1 |
| 2007/0005045 A1* | 1/2007 | Mintz et al. | 606/1 |
| 2007/0073137 A1* | 3/2007 | Schoenefeld | 600/407 |
| 2007/0142824 A1 | 6/2007 | Devengenzo et al. | |
| 2008/0147089 A1* | 6/2008 | Loh et al. | 606/130 |
| 2008/0281301 A1* | 11/2008 | DeBoer et al. | 606/1 |
| 2011/0023650 A1 | 2/2011 | Li et al. | |

OTHER PUBLICATIONS

Written Opinion dated Mar. 28, 2014 for corresponding International Application No. PCT/EP2012/068955.

International Preliminary Report on Patentability dated Apr. 21, 2014 for corresponding International Application No. PCT/EP2012/068955.

* cited by examiner

HANDLING DEVICE AND METHOD FOR OPERATING A HANDLING DEVICE

BACKGROUND

1. Field of the Disclosure

The disclosure relates to a handling device and a method for using different instruments with the aid of a receiving device of a handling device.

2. Discussion of the Background Art

Handling devices such as robots, comprise, e.g. on robot arms, receiving devices for receiving instruments, such as e.g. tools. In case of a robot, e.g. of the type used on the medical sector and particularly in surgery, said receiving devices will take up surgical instruments. In such a situation, it can be provided that a given receiving device will take up different instruments. This will involve an exchange of the instruments or tools.

For ensuring that, at a desired point of time, the correct instrument is connected to the receiving device, the instruments can be provided with passive markings such as e.g. inscriptions or the like. With the aid of pre-defined working instructions or a clearly defined working schedule, the required instrument, having been correspondingly marked or identified, will be connected to the receiving device by a user. In medical robots, the connecting of a surgical instrument is performed by a surgical assistant as prescribed by a surgical plan or as instructed by the operating surgeon. This approach is susceptible to faults and is not flexible either.

For avoidance of a wrong connection of instruments to a receiving device, it is further possible to provide unambiguous interfaces. In this case, the interfaces of the components are designed to the effect that only desired connections are possible. The interfaces thus comprise a mechanism which prevents a wrong connection. This approach is inflexible and allows for a mere limited number of connecting options, and, particularly, the approach can be varied only with considerable expenditure.

Further, in machine tools, it is known to provide an automatic changing of tools. For this purpose, the different tools and respectively instruments are kept available in a magazine. In a control unit of the machine tool, a defined working schedule has been preset. On the basis of the working schedule, an automatic changing of tools will be performed. This is achieved in that the machine tool has knowledge of which position of the magazine has which tool arranged in it. Such an automatic changing of tools can be realized only by use of complex devices. In the changing of instruments of a medical robot, such complexity is not practicable.

It is an object of the disclosure to provide a handling device wherein different instruments can be changed in a simple manner while the occurrence of faults is to be avoided. Further, it is an object of the disclosure to provide a method for operating such a handling device.

SUMMARY

The handling device according to the disclosure, which particularly is a robot such as e.g. a medical robot for preferred use in surgery, comprises at least one receiving device. The receiving device, arranged e.g. on a particularly multi-jointed robot arm, serves for receiving different instruments. Thus, with the aid of the receiving device, there can be fastened different instruments, such as tools, surgical instruments and the like, particularly at different times. Of course, it is also possible to connect intermediate elements to the receiving device, which then will have the instruments attached to them. For connecting different instruments to sais at least one receiving device, the receiving device and the instruments comprise mutually compatible connecting elements. The connecting elements are of the mechanical and optionally also electrical type, such as e.g. plugs and the like.

According to the disclosure, changeable and respectively activatable indicator devices are provided on the instruments. Said indicator devices are e.g. illuminants such as LEDs, a display or the like. With the aid of a control unit, the indicator device can be changed. For this purpose, the control unit is connected to the indicator devices of the instruments via electrical lines, by radio or the like. Particularly, the control unit is operative to control the indicator device in accordance with desired control data. The desired control data can be a current input by the user of the handling device, such as e.g. a surgeon. Further, a workflow plan can be stored in the control unit, which then, in accordance with a temporal process, will generate control signals for the indicator devices. An exchange of instruments and thus the changing of an indicator device can of course also be performed in dependence on defined events, such as e.g. that a specific instrument position has been reached, that the completion of a working step has been confirmed by a surgeon, or similar events, and the exchange can be combined e.g. with a workflow plan.

If the indicator device on the different instruments is realized in the form of one or a plurality of illuminants such as e.g. LEDs, the control unit will indicate a desired instrument by activation of the illuminant. A user, such as e.g. a surgical assistant, will then connect the indicated desired instrument to the receiving device. Due to the activated illuminant, it will be unambiguously clear which instrument shall be connected to the receiving device.

Additionally, also the receiving device can be provided with a changeable indicator device. In this case, when a changing of instruments is desired, the control unit will preferably activate the indicator device on the desired instrument as well as the indicator device on the receiving device. The user will thus clearly realize not only which instrument shall be used but also to which receiving device this instrument shall be connected. This is of advantage particularly if a handling device comprises a plurality of receiving devices or if a plurality of handling devices are arranged in the immediate vicinity to each other. In the latter case, control of a plurality of handling devices can be carried out by a common control unit.

For making it possible to perform a changing of instruments in a simple and safe manner, it is essential according to the disclosure that at least one of the component parts which are to be connected—and which, particularly in the above described preferred embodiment, are a receiving device and an instrument—is provided with an indicator device. Thus, in the above described surgical instrument, it would also be possible that the indicator device is provided on the at least one receiving device while the instrument is left without an indicator device.

For further enhancement of safety, it can be provided that an instrument is activated by the control unit. For this purpose, the instrument is provided with a corresponding activation device which can be an electronic circuit or an electronic component. Thereby, it can be ensured e.g. that only an instrument which has been activated in the above manner can be connected to the receiving device. The activation can also be performed in that, for instance, from an instrument holder containing the assortment of non-used instruments, an instrument is allowed to be collected only if it is activated. It is also possible to provide a mechanical activation means. This can be a pin, a bolt or the like which e.g. can be actuated or shifted only in the activated state of an instrument.

Particularly, it is preferred to provide activatable activation elements on the connecting elements of the receiving device and/or of the different instruments. Activation is performed via a control unit. Said activation elements can be mechanical or also electronic activation elements. Mechanical activation elements are particularly realized as pins, projections and the like which e.g. are allowed to be moved only in the activated state. Electronic activation elements can be realized e.g. by an exchange or request of codes or keys.

According to a preferred embodiment of the disclosure, the control unit is designed to have stored in it a workflow plan in which the temporal order of the exchanges of instruments is set. Such a workflow plan can be e.g. a planned procedural sequence of a surgical operation. This sequence is determined in the preparatory stages of the operation. Then, depending on the current progress of the operation, activation of the appropriate indicator device of the next required instrument will be performed via the control unit. Optionally, the control unit—in addition to, or instead of, a stored workflow plan—can comprise an input device or be connected to an input device. Via such an input device, a desired exchange of instruments can be activated. In a medical robot, this can be performed e.g. through input by the surgeon. Further, the input device can communicate a confirmation that a certain operational step has been concluded and that the next exchange of instruments is thus being initiated by the control unit.

In an inventive method for connecting instruments to a receiving device of a handling device, an indicator device arranged on the corresponding instrument will be activated by a control unit. The activation is performed via the control unit on the basis of a stored workflow plan and/or by means of an input device connected to the control unit. The exchange of instruments will then be carried out by a user, such as e.g. a surgical assistant, or optionally automatically.

Preferably, the method is advantageously refined as described above in the context of the handling device.

According to a particularly preferred embodiment, the handling device according to the disclosure and the method according to the disclosure can be applied in medical robots. Also in other types of robots, the handling device and the corresponding method are of advantage. Particularly in a manually guided, robot-assisted assembly of modules, the handling device of the disclosure and the corresponding method can be used with benefit. Particularly preferred is a corresponding use of such robots in the assembly of modules in outer space because, in this situation, work will have to be performed under extreme conditions, particularly under high time and cost pressure.

The disclosure will be explained in greater detail hereunder by way of preferred embodiments with reference to the drawings.

DETAILED DESCRIPTION OF THE PREFERRED EMBODIMENT

Figure 1:
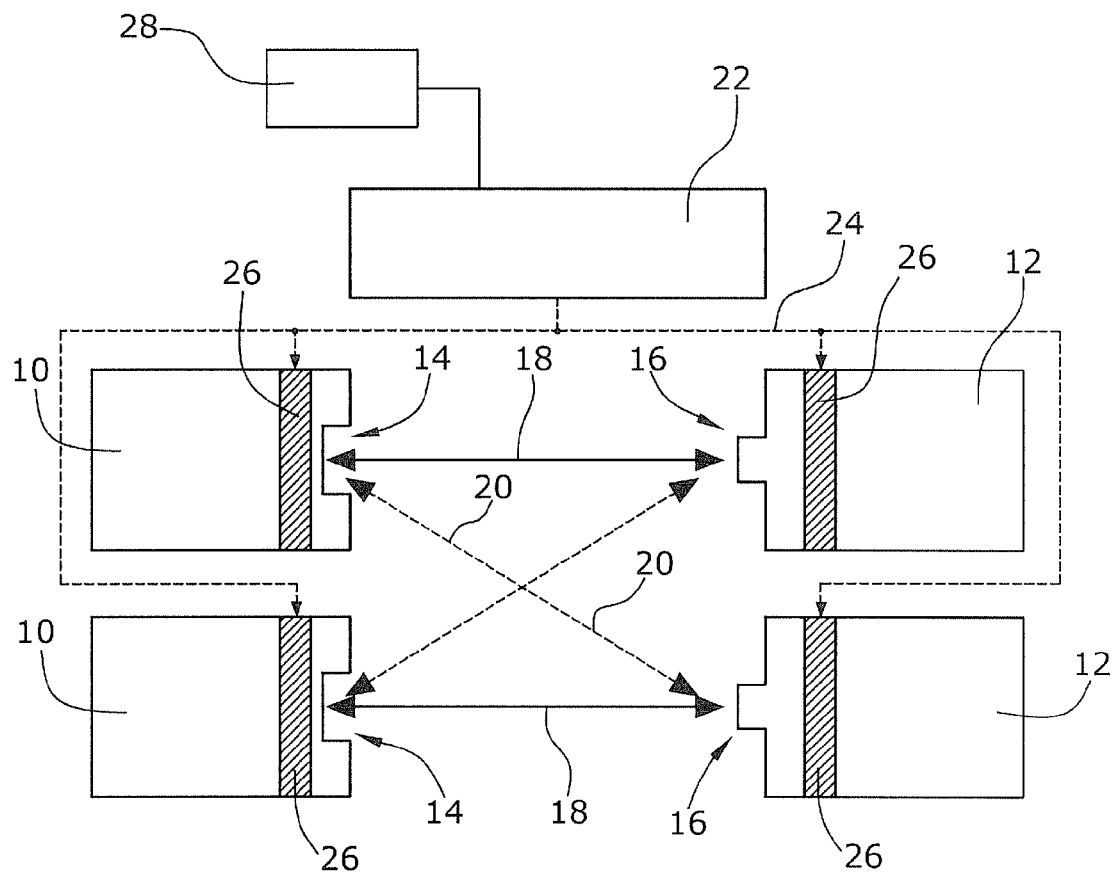
FIG. 1 is a schematic sketch illustrating an exchange of tools in a handling device.

The schematic sketch (FIG. 1) shows, by way of example, two components 10 which can be connected to two components 12. Herein, for instance, the components 10 are receiving devices, and the components 12 are instruments such as e.g. tools, surgical instruments, intermediate elements or the like. The receiving elements can be connected particularly to a robot. The components 10 comprise connecting elements, shown as recesses 14, which can be connected to connecting elements 16 schematically shown as projections on the components 12. In this arrangement, it is possible to connect one of the two components 10 to a respective one of the two components 12. The pairs of connecting elements 14, 16 herein are compatible. This allows for connections of one component 10 to a component 12 in the manner represented by the arrows 18 and 20.

Further, the handling device comprises a control unit 22 which, via lines 24 or also in a wireless manner, is connected to indicator devices 26. In the illustrated embodiment, a respective indicator device 26 is provided for each component 10, 12, said indicator device being e.g. an illuminant, a display or the like.

According to the disclosure, the indicator devices 26 can be activated by the control unit 22. Activation is carried out by a workflow program stored in control unit 22, or via an input device 28, comprising e.g. a keyboard, a joystick or the like, which is connected to control unit 22.

If, due to an input in the input device 28 and/or due to a stored workflow plan, there shall be established a connection of the upper component 10 in FIG. 1 to the upper component 12, the control unit 22 will control the two corresponding connecting elements 16 in such a manner that these will light up in the same color. A user of the handling device will thus unambiguously know which components shall be connected to each other for performing the next working step. A connection e.g. of the type shown by the interrupted arrows 20 is not desired and will not be realized. This prohibition can be additionally supported by providing an activation device, not shown, which is operative to avoid a connecting of components in the manner outlined by said arrows 20.

Figure 2:
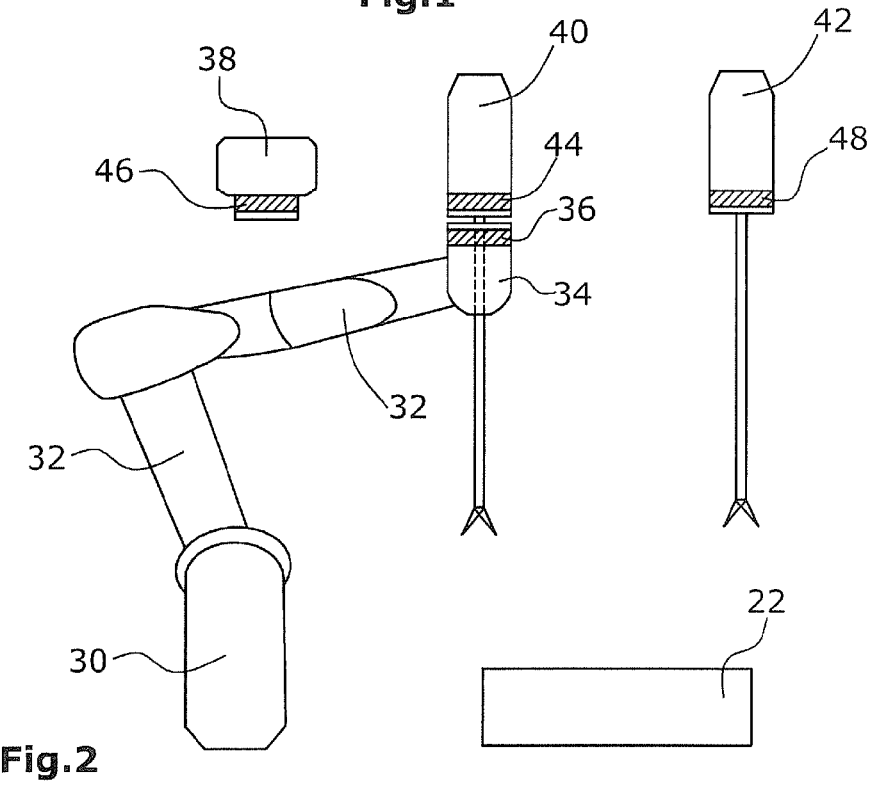
FIG. 2 is a schematic diagram illustrating an exchange of surgical instruments in a medical robot.

A medical robot as schematically shown in FIG. 2 can be designed in a corresponding manner. Herein, a base 30 of a robot is connected to a multi-jointed robot arm 32 which at distal end is connected to a receiving device 34. The latter is designed corresponding to the two components 10, 12 (FIG. 1) and comprises a connecting element, not shown, and an indicator device 36. In the illustrated embodiment, said receiving device 34 can be connected to three different surgical instruments 38, 40, 42. If, for instance, the existing instrument 40 shall be replaced by the instrument 38, the indicator device 44 of instrument 40 will be deactivated and the indicator device 46 of instrument 48 will be activated. In case of a color-based indication, the indicator device 36 of the receiving device will light up in the same color as the indicator device 46 of instrument 38.

The corresponding controlling of the indicator elements is performed via a control unit 22 which, as explained with reference to FIG. 1, can also be connected to an input device 20. Thus, the control unit 22, in accordance with a workflow plan which is influenced or activated e.g. by the progress of the surgical operation, will control the indicator devices 44, 46, 48 of the surgical instruments 38, 40, 42 in combination with the indicator device 36 of the receiving device 34.

In the illustrated embodiment, the indicator device 36 of the receiving device 34 could be omitted because only one receiving device is provided. If, however, the system is a robot system comprising a plurality of robot arms and thus also a plurality of receiving devices, the provision of a corresponding indicator device on the receiving device is suitable so as to ensure that the instrument will be connected to the correct, desired receiving device.

Figure 3A:
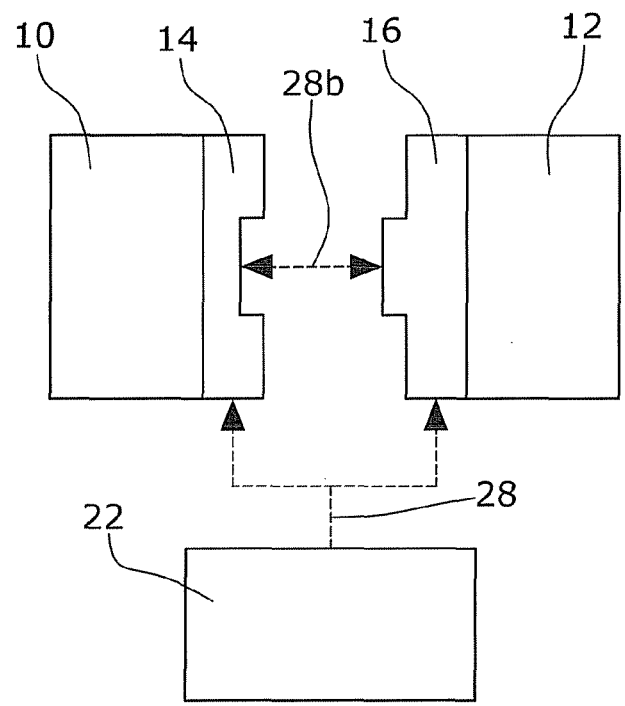
FIGS. 3a-3c show different embodiments of the design of electronic activation elements.
Figure 3B:
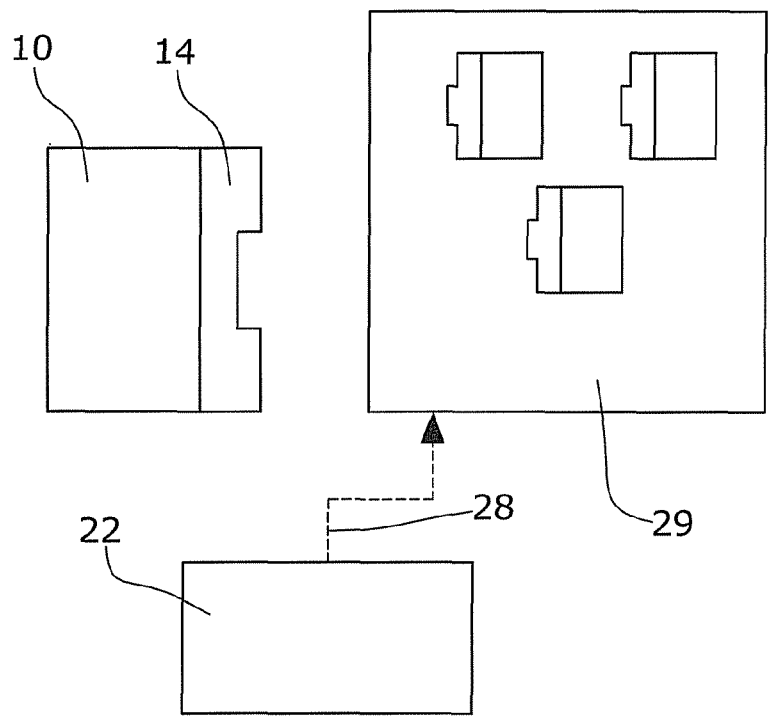
Figure 3C:
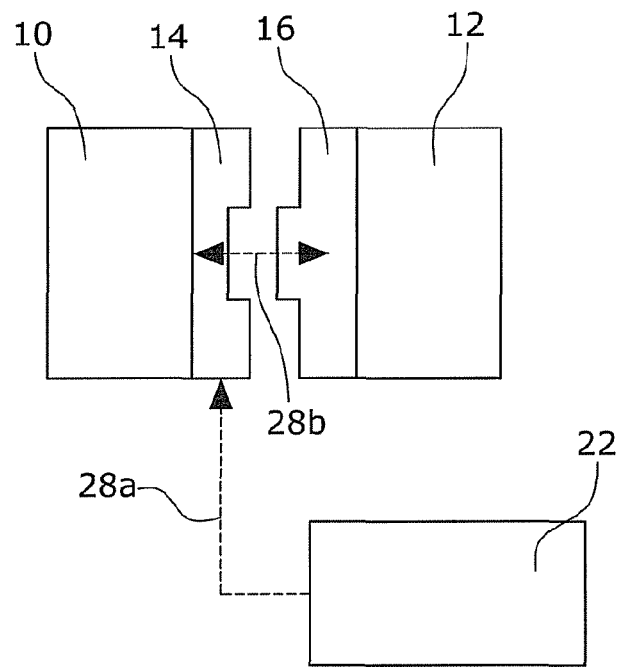

In FIGS. 3a-3c show various embodiments of activation devices to be activated by the control unit 22. According to a general design, the control unit 22 communicates with the activation device 14 arranged on the connecting element of robot 10, and with the activation device 16 arranged on the instrument. A safe exchange of tools according to the disclosure will proceed as follows: The control unit will activate the desired tool with the aid of the activation device 16 and will communicate to the activation device 14 on the robot which tool has been activated. When the activation devices are to be connected, they will realize whether or not they match with each other. Only connecting elements having matching activation devices are allowed to be connected to each other. Whether or not a connection has been achieved will be communicated to the control device by activation element 14 and/or activation element 16 via a communication device 28. In case of a connected state, said communication can also be performed from 16 to 14 via 28b.

FIG. 3b shows a variant of the disclosure wherein the instruments from which to choose are arranged in a rack 28 which includes the activation elements assigned to the instruments. In this case, the control unit 22 will communicate via 28 with said rack for activating the desired tool. Only the activated tool can be taken from the rack by the user. In this case, no activation element is required on the connecting element of the robot.

FIG. 3c shows a variant of the disclosure wherein the control unit will directly communicate only with the activation element 14 on robot 10. For performing a safe exchange of tools, control unit 22 will communicate to activation element 14 which tool shall be connected to the robot. Thereafter, only the instrument having the corresponding activation element 16 can be connected at the connecting element 14 of robot 10. In order to detect the corresponding activation element, an exchange of information 28b takes place between activation element 16 on the instrument and the activation element 14 the on robot (However, there is no need for a direct communication between the instrument and the control unit).

Hereunder, various variants of the activation elements will be explained.

One possible variant is the activation by a specific code which can be transmitted per software, electric signals or mechanical (key-lock).

A variant of FIG. 3a resides in a corresponding activation by transmission of a key (code), which is valid only for the desired point of time and for a specific connection, from the control unit 22 to the activation element 14 to the activation element 16 on the instrument. A connection will be established if, by exchanging the keys via data communication 28b, a congruence is detected.

Figure 4:
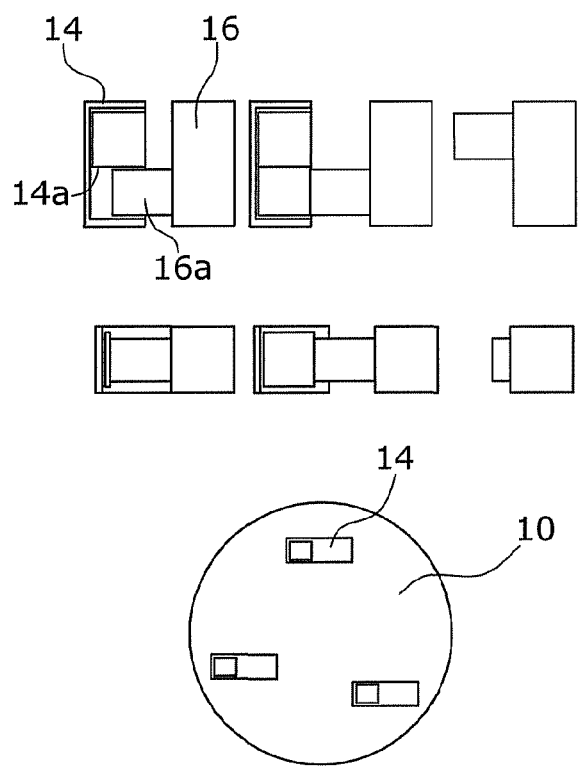
FIG. 4 is a schematic view of an embodiment of a mechanical design of activation elements.

A possible electromagnetic variant is shown in FIG. 4. The activation element 14 consists of a recess 14b having a pin 14a arranged in it. The position of the pin within the recess can be changed with the aid of a control unit. This can be carried out horizontally (variant a) or vertically (variant b). The corresponding activation element 16 comprises a projection 16a which can be inserted into the recess of activation element 14 only exactly in a specific position of pin 14a. Only in this case, a connection can be established.

Said pin can assume at least two different known positions. However, also a quasi stepless adjustability is possible. The number of differentiating positions is determinant of the number of possible connection variants between the activation elements. By arranging a plurality of activation elements at a connection 10, this number can be further increased. The communication variant belonging to this embodiment corresponds to the one shown in FIG. 3c, the communication 28b being realized mechanically.

What is claimed is:

1. A handling device, comprising:
   a receiving device for receiving different instruments,
   the receiving device and the different instruments having mutually compatible connecting elements,
   changeable indicator devices provided on the instruments, and
   a control device connected to the indicator devices for changing the indicator devices in accordance with desired control data, wherein, in addition to the indicator devices, also the receiving device is provided with an indicator device, and wherein, for indicating a required connection, the indicator device of the receiving device and the indicator device of the requested instrument comprise corresponding indicators.

2. The handling device according to claim 1, wherein the indicator devices comprise illuminants.

3. The handling device according to claim 1, wherein the indicator devices comprise a display.

4. The handling device according to claim 1, wherein the connecting elements comprise activation elements to be activated by the control unit so that a connection to the receiving device is possible only in the activated state of the activation element.

5. The handling device according to claim 1, wherein, in the control unit, a workflow plan can be pre-stored in which the temporal order of the changes of instruments is defined.

6. The handling device according to claim 1, wherein the control unit is connected to an input device for inputting a desired change of instruments.

7. A method for connecting instruments to a receiving device of a handling device, comprising:
   activating, by means of a control unit and on the basis of a stored workflow plan and/or by use of an input device, an indicator device arranged on an instrument and an indicator device arranged on the receiving device, the indicator device of the receiving device and the indicator device of the instrument comprising corresponding indicators; and
   connecting said instrument to the receiving device based on the corresponding indicators.

8. A handling device, comprising:
   a receiving device for receiving different instruments,
   the receiving device and the different instruments having mutually compatible connecting elements,
   changeable indicator devices provided on the instruments, and
   a control device connected to the indicator devices for changing the indicator devices in accordance with desired control data, wherein the connecting elements comprise activation elements to be activated by the control unit so that a connection to the receiving device is possible only in the activated state of the activation element.

9. A handling device, comprising:
   a receiving device for receiving different instruments,
   the receiving device and the different instruments having mutually compatible connecting elements,
   changeable indicator devices provided on the instruments, and a control device connected to the indicator devices for changing the indicator devices in accordance with desired control data, wherein, in the control unit, a workflow plan can be pre-stored in which the temporal order of the changes of instruments is defined.

\* \* \* \* \*